US00PP34798P2

(12) United States Plant Patent
Whitcomb

(10) Patent No.: US PP34,798 P2
(45) Date of Patent: Dec. 6, 2022

(54) CHERRY LAUREL PLANT NAMED 'WHIT XXXIV'

(50) Latin Name: *Prunus caroliniana*
Varietal Denomination: 'Whit XXXIV'

(71) Applicant: Lacebark, Inc., Stillwater, OK (US)

(72) Inventor: Carl E. Whitcomb, Stillwater, OK (US)

(73) Assignee: Lacebark, Inc., Stillwater, OK (US)

( * ) Notice: Subject to any disclaimer, the term of this patent is extended or adjusted under 35 U.S.C. 154(b) by 0 days.

(21) Appl. No.: 17/803,384

(22) Filed: Jun. 13, 2022

(51) Int. Cl.
*A01H 5/12* (2018.01)
*A01H 6/74* (2018.01)

(52) U.S. Cl.
USPC ..... Plt./226
CPC ..... *A01H 6/7427* (2018.05)

(58) Field of Classification Search
USPC ..... Plt./226
CPC ..... A01H 6/7427; A01H 5/02; A01H 5/12
See application file for complete search history.

(56) References Cited

U.S. PATENT DOCUMENTS

PP6,350 P 10/1988 Hilger

*Primary Examiner* — Keith O. Robinson
(74) *Attorney, Agent, or Firm* — Jeffrey L. Streets; Streets Lawfirm P.C.

(57) ABSTRACT

A new and distinct variety of cherry laurel, *Prunus caroliniana*, with exceptional tolerance to cold, down to −18 F, which has been given the cultivar name 'Whit XXXIV' is characterized by an upright growth habit with dense broad flat evergreen foliage making it effective as a visual barrier as well as noise reduction.

4 Drawing Sheets

Latin name: *Prunus caroliniana.*
Varietal denomination: 'Whit XXXIV'.

BACKGROUND OF THE INVENTION

Field of the Invention

The present invention relates to a new and distinct variety or cultivar of the native evergreen shrub or small tree, *Prunus caroliniana*, commonly known as cherry laurel or Caroliniana cherry laurel.

Description of the Related Art

Cherry laurel is a large evergreen shrub or small tree native over a wide range of the southeastern USA. In Trees of Northern Florida by Kurz and Godfrey, 1962, they note "cherry laurel is so widely used as an ornamental and it readily becomes naturalized in woodlands that its natural range is difficult to establish". Grows well in full sun or shade, with dense branching and glossy, dark green foliage and adaptable over a wide assortment of soils and growing conditions. Leaves are alternate, persistent, leathery, dark glossy green above and light green below, supported by a short, stout petiole. Grows mostly as a single stem small tree unless pruned at a young age to stimulate multiple stems. Responds well to pruning and is often used as an evergreen screen or hedge. Many species of birds eat the fruits and disperse seeds, where seedlings can become weedy.

Cherry laurel is effective as a hedge or screen in reducing noise from adjacent areas. For example, in 1973, Whitcomb and Stowers studied the effectiveness of a number of species as hedges using a sound generator, lawn mower and automobile. They found that a broadleaved evergreen hedge was most efficient at reducing noise, giving a 5 to 7 decibel reduction in sound 10 or 20 feet behind the hedge. In the study, width of the hedge was less important than leaf characteristics of the species, particularly with low frequency sounds. A reduction of 5 decibels amounts to a reduction of about 50% in the apparent loudness of a sound.

U.S. Plant Pat. No. 6,350 by Hilger describes a cherry laurel with oblong lanceolate leathery leaves distinguished by having a rich golden yellow color in green leaves. Originated as a sport in Largo, Fla. There is no mention of cold tolerance or range of adaptability.

In central Oklahoma where this research was conducted and a high population of whitetail deer, cherry laurel is resistant to foliar grazing, likely due to the bitter taste and presence of prussic acid (cyanide). On the other hand, white tail deer can severely damage or destroy small cherry laurel trees during the fall rutting season as the thin bark is easily torn from the main stem.

BRIEF SUMMARY OF THE INVENTION

The plant of the present invention is a new and distinct variety of cherry laurel, *Prunus caroliniana*, which has been given the cultivar name 'Whit XXXIV'. It is characterized by an upright growth habit with dense evergreen foliage. Leaves of this small tree emerge with variable areas of pinkish-tan, transitioning to light green then dark green and developing a shiny upper surface. New leaves appear in spring and remain on the plant a full year, finally dropping after full development of new growth the following season. With pruning or shearing, secondary branches emerge quickly forming a dense hedge, effective as a visual screen. Because of the broad flat leaves, research has shown that cherry laurel effectively reduces automobile and lawnmower noise during all seasons. A typical cherry laurel screen about three feet thick reduced noise by 5 decibels or about 50%. My new variety, 'Whit XXXIV' with especially dense foliage is expected to provide equal or better sound reduction compared to the species in general.

The new invention cherry laurel named 'Whit XXXIV' was developed from a multi-generational seedling population, beginning with seeds first collected in 1988 in northern Virginia which resulted in about 250 seedlings. A severe winter four years later in northern Oklahoma killed all of the seedlings but three. Subsequent seedlings from those three especially cold tolerant plants resulted in even more cold tolerant plants. In 2015, seedlings from the most cold-tolerant plants to date resulted in 43 seedlings. During February 2021, when plants were 6 years old and temperatures near Stillwater Okla. dropped to −1 F, then −18 F, then −6 F, during a period when temperatures remained below freezing for 15 days, most of the seedlings were killed or severely damaged, but one survived with no damage, retaining all leaves, no scorched leaf margins and no twig dieback. Spring growth proceeded normally and cuttings from this specimen rooted well and made good growth the rest of the growing season. This especially cold tolerant specimen was given the cultivar name 'Whit XXXIV'.

DETAILED BOTANICAL DESCRIPTION

The following is a botanical description of the new and distinct variety of cherry laurel, *Prunus caroliniana* which has been given the variety name 'Whit XXXIV'. Specific color designations set forth by number designation are in accordance with The Royal Horticulture Society Colour Chart (1966). General color recitations are consistent with ordinary American color terminology.

The plant:

*Type*.—Broadleaf evergreen shrub or small tree.

*Classification*.—Cherry laurel or Caroliniana cherry laurel, *Prunus caroliniana*.

*Growth habit*.—Upright growing plant with dense foliage, typically with a single stem and no secondary branches or suckers near the base unless pruned at a young age.

*Shape, height and spread*.—Shape is cylindrical to a height of 20 feet with age and spread of 8 to 12 feet.

Figure 1:
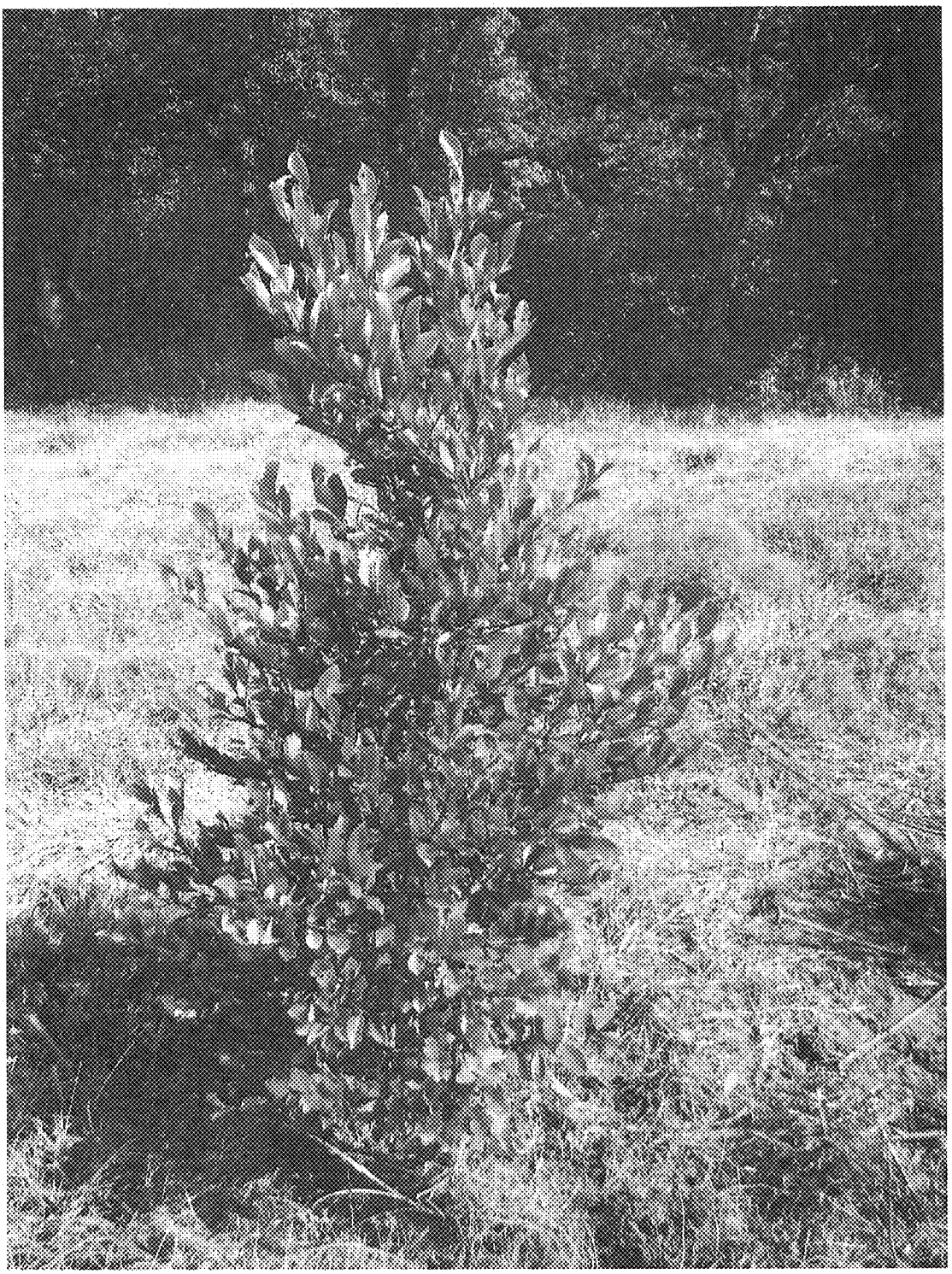
FIG. 1 is a full color view of the new and distinct variety of cherry laurel plant named 'Whit XXXIV' showing upright growth habit with dense branching and glossy green foliage color at age six years. This is the appearance of the new and distinct variety of cherry laurel plant named 'Whit XXXIV' as photographed in March 2021 following a winter cold temperature period during February 2021 with 15 days not rising above freezing and the most severe cold −1 F, −18 F, and −6 F. during that period.

*Origin*.—The new invention cherry laurel named 'Whit XXXIV' was developed from a multigenerational population, beginning with seeds collected in 1988 in northern Virginia, which resulted in about 250 seedlings. A severe winter four years later at my research site in northern Oklahoma killed 247 seedlings, while the remaining three were undamaged and grew well. Subsequent seeds from those three most cold tolerant plants resulted in even more cold tolerant plants during the interim 27 years. In 2015, seeds from the most cold-tolerant plants up to that date resulted in 43 seedlings which were planted in a field near Stillwater, Okla. During February 2021 when these 43 seedlings were six years old, temperatures at my farm near Stillwater, Okla. remained below freezing for 15 days, with the most severe cold on successive nights being −1 F, followed by −18 F, then −6 F. Most of the 43 seedlings were killed or severely damaged, but one survived with no damage, retaining all leaves, no scorched leaf margins and no twig dieback as shown in FIG. 1. Spring growth on the surviving plant proceeded normally and cuttings from this specimen rooted well and made good growth the rest of the growing season. This especially cold tolerant specimen was given the cultivar name 'Whit XXXIV'.

*Propagation*.—Propagation is by softwood to early semi hardwood cuttings of current season's growth. Cuttings have been taken and the resulting plants have features identical to the parent.

*Hardiness*.—The new and distinct variety of cherry laurel named 'Whit XXXIV' is exceptionally cold hardy having no injury from an exceptionally severe period during February 2021 when temperatures remained below freezing for 15 days, with extremes of −1 F, −18 F and −6 F in succession.

*Vigor and growth rate*.—Growth rate is moderate relative to other small trees, reaching a height of 6 to 9 feet in 8 years, depending on soil conditions and moisture.

*Pests and disease*.—Resistant to grazing by white tailed deer, even under high deer population. However, the thin bark is vulnerable to damage during the fall rutting season by white tailed deer. Grasshopper damage is sometimes observed on parts of individual leaves, but damage is minor. Foliage damage may occur from fall webworms (*Hyphantria cunea*) and bagworms (*Thyridopteryx ephemeraeformis*). No leaf spot disease has been observed on any of the seedling grown during the 34 years of this research.

*Comparison to a known variety*.—U.S. Plant Pat. No. 6,350 (Hilger) describes a variety of Cherry Laurel as having a distinct variegation of golden yellow in green leaves. The new and distinct variety of cherry laurel named 'Whit XXXIV' is green, as shown in the referenced Figures, with the only exception being very young growth which is pinkish-tan quickly transitioning to light green then dark green.

*Comparison of the plant to the seedlings originating in the wild in northern Virginia.*—The new and distinct variety of cherry laurel named 'Whit XXXIV' is similar in general appearance to perhaps 1,000 seedlings or more from multiple aged seedlings from the same genetic line which originated in northern Virginia, except that 'Whit XXXIV' is more dense and far more cold-tolerant. Compared to the 43 seedlings that were growing in the same row in 2021 when the severe freeze occurred, appearance is similar to the few other survivors, except that 'Whit XXXIV' is more dense and was not affected by the cold that killed or severely damaged other plants in that row.

The flowers: Flowering period is early spring following emergence of new growth. Flower development begins in axils of old leaves in short racemes, but abort about the time flower buds are observed. During the 34 years of this research, typical cherry laurel seedlings begin flowering at about age four years. The new variety named 'Whit XXXIV' has produced no flowers or fruits during ages 5, 6, and 7. Whether this feature of no fruit development will remain as the tree ages is unknown.

The foliage:

*The foliage and form.*—Growth is upright with dense branching and foliage. Old leaves remain on the plant after new spring growth and slowly drop during the growing season as new growth reduces light below the compensation point.

Figure 2:
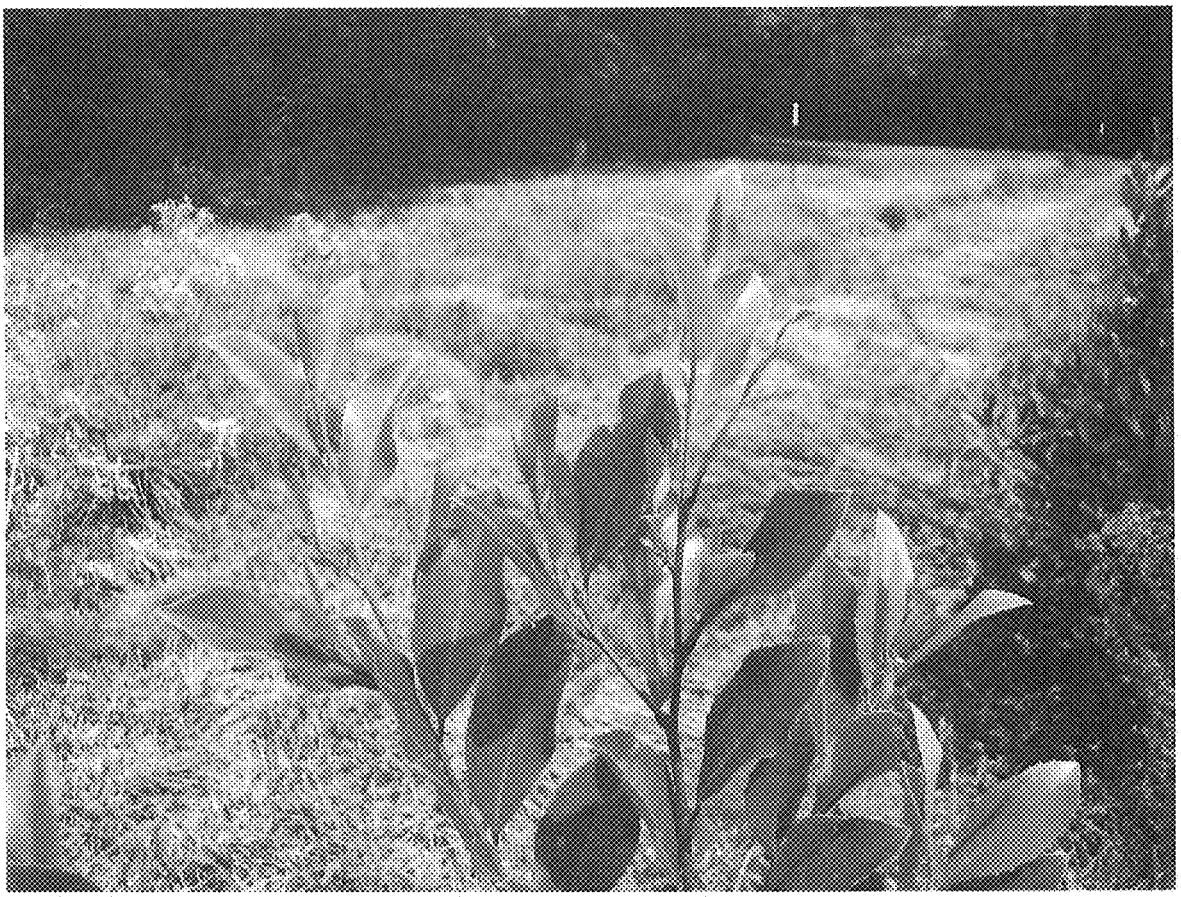
FIG. 2 is a full color view of emerging spring growth of the new and distinct variety cherry laurel plant named 'Whit XXXIV' showing brief pinkish-tan color of new foliage that quickly transitions to light green then dark green with glossy leaf surface.

*Leaf arrangement.*—Alternate and simple, spaced variably around the stem with variable distance between leaves. The number of leaves per branch is widely variable, from about 4 to 10 on a short single branch to 20 to 30 on a branch complex (See FIG. 2). In FIG. 2, there is one central branch that is developing secondary branches as it grows, in this case showing four branches in the photo, and with the lower branch also developing a secondary branch. The branch at the left of the photo also has four branches, but none of those are yet developing second branches (which maybe should be referred to as tertiary branches). It is this free and irregular branch development that lead to the dense foliage on the plant that is so effective in reducing noise and making an effective visual screen.

*Leaf shape.*—Leaf blades are oval to elliptical, typically 1.5 to 2.75 inches long by 0.75 to 1.25 inches wide, bases are mostly cuneate with a short, stout petiole typically about 53 A or B when in full sun, but irregularly lighter when shaded, the apex acute or short-acuminate, the tips sharp. Leaf margins range from smooth or variably shallowly serrate. The strong petiole allows limited flexibility. Petiole is similar color to the developing leaf surface when young, becoming about red-purple about 72 A or B on leaves with moderate to high sun exposure, but lighter about 72 C or D in shade.

*Leaf surface and color.*—Glabrous, with color variable among upper surface of new leaves on a stem of current seasons growth, beginning about 164 A or B, quickly transitioning to about 144 A or B, then to about 137 B, C or D, then at maturity in mid-season about 137 A or B. (see FIG. 2 or 3). Lower leaf surface is a slight reddish color when young (nothing matches), then as leaves age, color transitions to about 145 D, then with maturity to about 145 B or C.

*Leaf texture.*—Upper surfaces are smooth, glabrous, becoming stiff and leathery with maturity. The texture of the lower leaf surface is smooth, glabrous.

*Leaf size.*—Variable, ranging from about 1.5 to 2.75 inches long and 0.75 to 1.25 inches wide.

Figure 3:
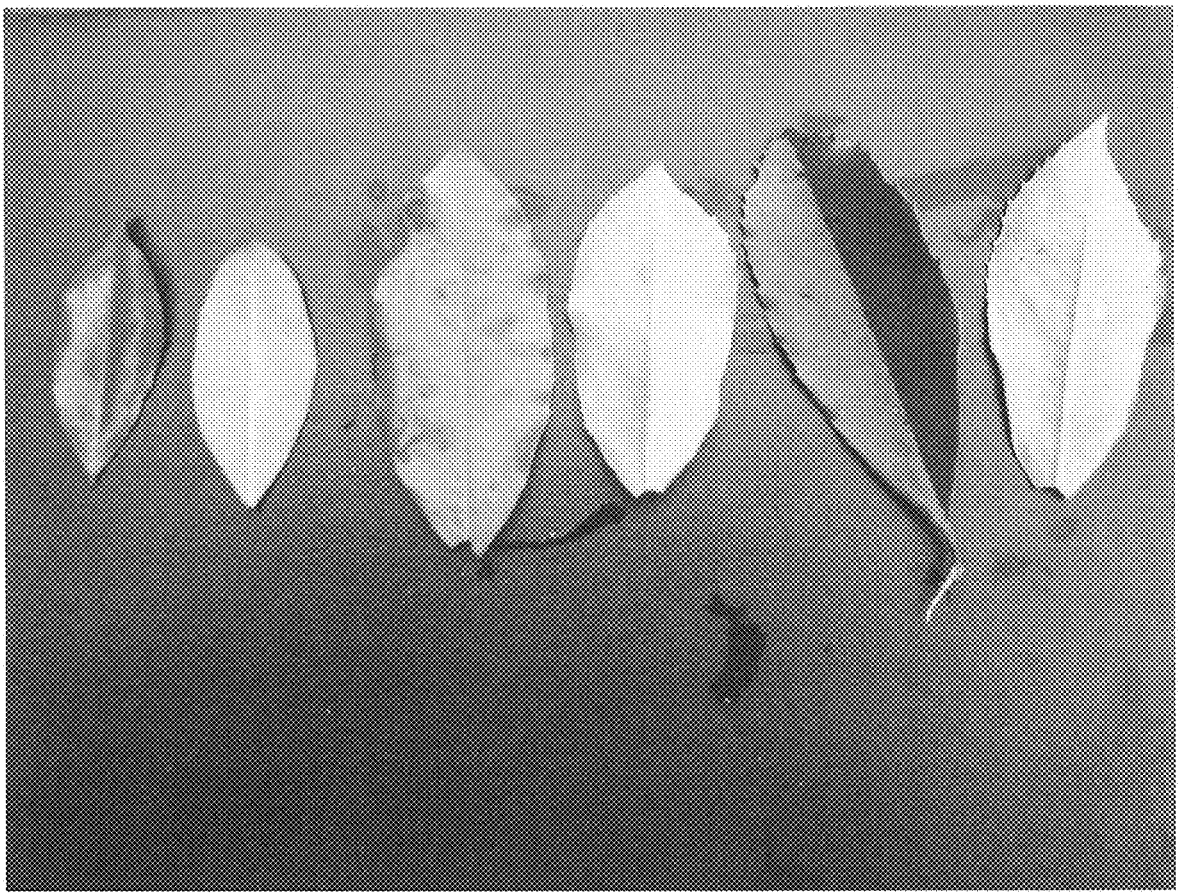
FIG. 3 is a full color view of typical upper and lower leaf surfaces of the new and distinct variety cherry laurel named 'Whit XXXIV' showing young leaves (the two leaves on the left), leaves of intermediate development (the two leaves in the middle) and mature leaves from the previous growing season (the two leaves on the right).

*Leaf margin.*—Variable, some leaves have distinct shallowly serrate margin as shown on the mature leaf in FIG. 3 (the two leaves on the right), while others have an entirely smooth margin as shown on the leaf of intermediate age in FIG. 3 (the two leaves in the middle) and all six leaves in FIG. 3 came from the same branch.

*Leaf venation.*—The venation pattern of the leaf is parallel, sometimes called nerved, but is nearly obscure visually, as shown in FIG. 3.

*Leaf fragrance.*—Leaf when crushed or broken has a faint cherry odor, more intense in young leaves, less so with older leaves, but variable. No attempt was made to quantify the variation in fragrance of various aged leaves.

The branches and bark:

*Branch and bark color.*—Current season's stems are briefly about 48 C or D, soon transitioning to about 53 A, then approaching end of first growing season about 176 A and finally when stems reach about 0.5 inches or larger, near black, slightly lighter than 202 A (but no good match) with transverse lenticels.

Figure 4:
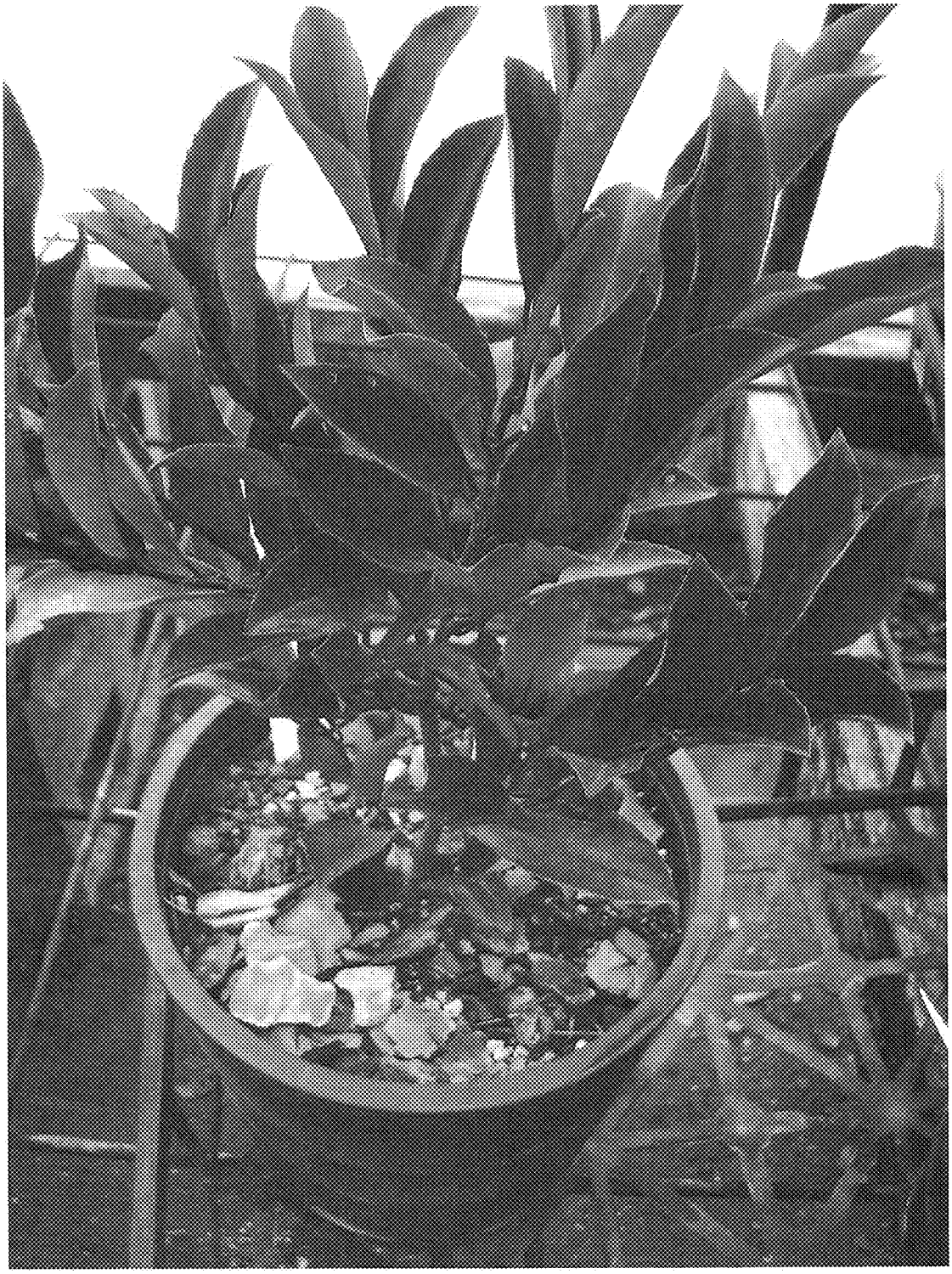
FIG. 4 is a full color view of a plant propagated asexually from the new and distinct variety cherry laurel named 'Whit XXXIV' as it appears near the end of the first growing season in a one-gallon container.

*Branching habit.*—Branching habit is irregular and with variable branching as shown in FIGS. 1 and 2, creating a dense foliage mass, difficult to quantify. Branching occurs near the base of the plant and continues with asexual propagated offspring as shown in FIG. 4. This branching habit is highly desirable and novel relative to the large numbers of other seedling Cherry Laurel plants grown during the lengthy, multi-year study. This feature is especially useful in blocking noise and wind, thereby avoiding the Venturi effect of wind blowing through an opening between the soil surface and the lower branches. Branches are flexible when young becoming stronger with age, but, not brittle or subject to breakage even when stems reach an inch or more in diameter. Branches are variable in diameter, as shown in FIG. 2, from very small at an early age becoming progressively larger with age.

*Number of branches.*—An attempt was made to count the number of branches on the plant, but as is clearly visible in FIG. 1, nearly impossible to do even with marking each branch counted to avoid repeat counting. As shown in FIG. 2, internode length is highly variable, and has little practical value in trying to describe this unique plant.

I claim:

1. A new and distinct variety of cherry laurel, *Prunus caroliniana* plant named 'Whit XXXIV', substantially as illustrated and described herein.

* * * * *